US008858610B2

United States Patent
Brown et al.

(10) Patent No.: US 8,858,610 B2
(45) Date of Patent: Oct. 14, 2014

(54) FORCED DEPLOYMENT SEQUENCE

(75) Inventors: Harold A. Brown, Seattle, WA (US);
Eric J. Davis, Bothell, WA (US);
Michelle L. Gendron, Flagstaff, AZ
(US); John L. Loewen, Parks, AZ (US);
Clare R. Long, Edmonds, WA (US);
Justin W. Sokel, Flagstaff, AZ (US);
Joseph P. Sullivan, Issaquah, WA (US);
Markus Wierzoch, Seattle, WA (US)

(73) Assignee: W. L. Gore & Associates, Inc., Newark, DE (US)

( * ) Notice: Subject to any disclaimer, the term of this patent is extended or adjusted under 35 U.S.C. 154(b) by 783 days.

(21) Appl. No.: 12/689,104

(22) Filed: Jan. 18, 2010

(65) Prior Publication Data

US 2010/0211052 A1   Aug. 19, 2010

Related U.S. Application Data

(60) Provisional application No. 61/145,693, filed on Jan. 19, 2009.

(51) Int. Cl.
| | |
|---|---|
| *A61F 2/06* | (2013.01) |
| *A61M 31/00* | (2006.01) |
| *F16G 11/04* | (2006.01) |
| *A61F 2/95* | (2013.01) |

(52) U.S. Cl.
CPC ............... *A61F 2/95* (2013.01); *F16G 11/048* (2013.01); *A61F 2002/9505* (2013.01); *A61F 2002/9511* (2013.01); *A61F 2002/9517* (2013.01)
USPC .......................................... 623/1.11; 604/500

(58) Field of Classification Search
CPC .............. A61F 2002/9511; A61F 2/95; A61F 2002/9517; A61F 2002/9505
See application file for complete search history.

(56) References Cited

U.S. PATENT DOCUMENTS

| | | | |
|---|---|---|---|
| 1,851,314 A | 5/1929 | Knoche | |
| 3,625,451 A | 12/1971 | Anderson | |
| 4,655,246 A | 4/1987 | Phlipot et al. | |
| 5,554,183 A | 9/1996 | Nazari | |
| 5,707,376 A | 1/1998 | Kavteladze et al. | |
| 5,776,141 A | 7/1998 | Klein | |
| 5,776,186 A | 7/1998 | Uflacker | |
| 5,782,909 A | 7/1998 | Quiachon et al. | |
| 5,843,162 A | 12/1998 | Inoue | |
| 6,143,021 A | 11/2000 | Staehle | |
| 6,524,335 B1 | 2/2003 | Hartley et al. | |
| 6,527,779 B1 | 3/2003 | Rourke | |
| 6,705,563 B2 * | 3/2004 | Luo et al. ...................... 242/557 |
| 6,743,210 B2 | 6/2004 | Hart et al. | |
| 6,755,854 B2 | 6/2004 | Gillick et al. | |
| 6,866,669 B2 | 3/2005 | Buzzard et al. | |

(Continued)

FOREIGN PATENT DOCUMENTS

| | | |
|---|---|---|
| GB | 2344054 | 5/2000 |
| JP | 2003/509158 | 3/2003 |

(Continued)

*Primary Examiner* — Gary Jackson
*Assistant Examiner* — Scott T Luan
(74) *Attorney, Agent, or Firm* — Gilbert R. Gabo

(57) ABSTRACT

A fixed sequence activation handle is described that forces a predetermined activation sequence. Such handles are suitable for use in the delivery of medical devices or for other application that require a fixed sequence of activations.

11 Claims, 13 Drawing Sheets

(56) References Cited

U.S. PATENT DOCUMENTS

| | | |
|---|---|---|
| 6,884,259 B2 | 4/2005 | Tran et al. |
| 6,926,732 B2 | 8/2005 | Derus et al. |
| 6,939,352 B2 | 9/2005 | Buzzard et al. |
| 7,033,368 B2 | 4/2006 | Rourke |
| 7,052,511 B2 | 5/2006 | Weldon et al. |
| 7,066,951 B2 | 6/2006 | Chobotov |
| 7,122,050 B2 | 10/2006 | Randall et al. |
| 7,147,657 B2 | 12/2006 | Chiang et al. |
| 7,198,636 B2 | 4/2007 | Cully et al. |
| 7,208,003 B2 | 4/2007 | Davis et al. |
| 7,611,528 B2 | 11/2009 | Goodson et al. |
| 2002/0151953 A1 | 10/2002 | Chobotov et al. |
| 2003/0098383 A1 | 5/2003 | Luo et al. |
| 2004/0138734 A1 | 7/2004 | Chobotov et al. |
| 2005/0080476 A1 | 4/2005 | Gunderson et al. |
| 2006/0004433 A1 | 1/2006 | Greenberg |
| 2006/0155366 A1* | 7/2006 | LaDuca et al. ............... 623/1.23 |
| 2007/0100427 A1 | 5/2007 | Perouse |
| 2007/0249980 A1 | 10/2007 | Carrez et al. |
| 2008/0027529 A1 | 1/2008 | Hartley et al. |
| 2009/0082844 A1 | 3/2009 | Zacharias et al. |
| 2010/0016943 A1* | 1/2010 | Chobotov .................... 623/1.11 |

FOREIGN PATENT DOCUMENTS

| | | |
|---|---|---|
| JP | 2004/512867 | 4/2004 |
| WO | 97/48350 | 6/1997 |
| WO | 00/13613 | 3/2000 |
| WO | 01/21109 | 3/2001 |
| WO | 02/28317 | 4/2002 |
| WO | 2006/007389 | 1/2006 |
| WO | 2007/092354 | 8/2007 |

* cited by examiner

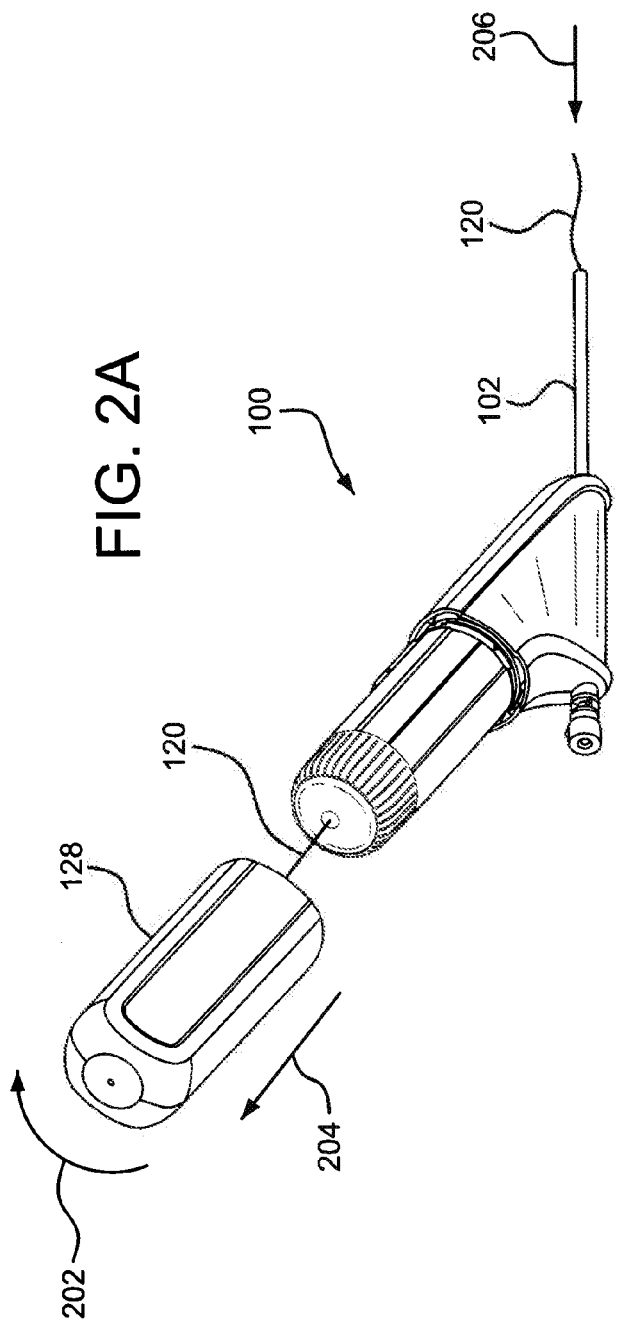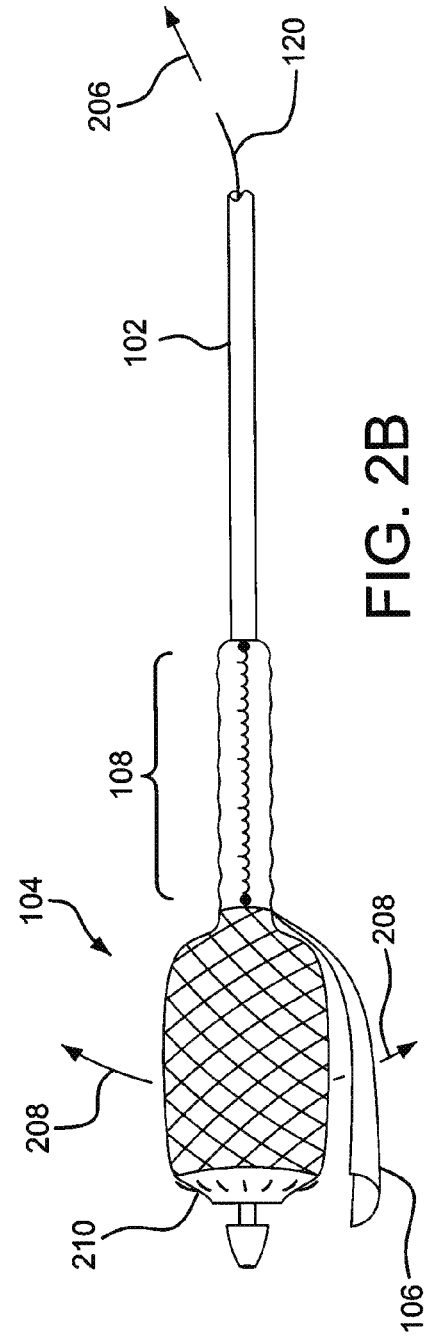

FORCED DEPLOYMENT SEQUENCE

CROSS-REFERENCE TO RELATED APPLICATIONS

This application claims benefit to U.S. Provisional Patent Application Ser. No. 61/145,693 filed Jan. 19, 2009, which is incorporated by reference herein for all purposes.

BACKGROUND OF THE INVENTION

1. Field of the Invention

The invention relates to a tool having a fixed sequence of activation steps. In particular the invention relates to medical device deployment handles that intend to eliminate practitioner errors of delivery sequence in deployment of a medical device.

2. Discussion of the Related Art

Endovascular medical devices that require a specific series of steps to complete the delivery are known in the art. For example the vascular prosthesis disclosed in U.S. Pat. No. 5,554,183 to Nazari has several control lines that are required to be activated in a particular sequence to affect proper deployment of the device. Nazari does not disclose a tool or operational handle that fail-safes the deployment sequence. Similar medical devices requiring a specific sequence of control line manipulations for proper deployment are disclosed in WO 97/48350 to Lauterjung and in U.S. Pat. No. 5,776,186 to Uflacker. Neither of these references discloses a tool or operational handle that would force the proper sequence of pull line manipulations.

There are a variety of medical device delivery handles, tools, aids, etc. used to implant endovascular devices. Examples of such delivery tools are used in steerable catheter systems, where one or more pull lines act as tendons. When pulled, the pull line deflects a portion of the catheter (normally the far distal end). The deflection of the catheter allows the precise navigation of the catheter through complex vasculature. Other medical device delivery handles provide a mechanical advantage to the pulling of a tether line or retraction sheath, used with self-expanding intravascular devices such as stent grafts. See for example U.S. Patent Application 2005/0080476 to Gunderson et al., for a handle that provides a mechanical pull advantage. Other embodiments of tools used to deliver implantable medical devices include simple luer-lock fittings that have pull lines attached to luer members. When a member is removed from the luer fitting the pull line is activated. See for example U.S. Patent Application 2002/0151953 to Chobotov et al. As typical in the art, the luer-lock and member arrangement as disclosed by Chobotov et al. are not interlocked; that is the multiple activation cords/rods can be activated in any sequence. In such non-interlocked systems, training, visual aids and labeling are typically used to encourage the proper delivery sequence. Despite the substantial efforts used to encourage the proper step sequencing, inadvertent user errors do occur.

SUMMARY OF THE INVENTION

The invention provides an interlocked control handle that forces a predetermined activation sequence. Control handles according to the present invention are suitable for use in the delivery of medical devices.

In particular the present invention provides a fixed sequence activation system, comprising at least a first removable member attached to a distally extending line for communication with a remotely located deployable device; and a second member attached to a distally extending line for communication with a remotely located deployable device to provide a fixed sequence activation of the deployable device.

Additional features and advantages of the invention will be set forth in the description or may be learned by practice of the invention. These features and other advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The accompanying drawings are included to provide a further understanding of the invention and are incorporated in and constitute a part of this specification, illustrate embodiments of the invention and together with the description serve to explain the principles of the invention.

In the drawings:

FIGS. 2A and 2B show perspective views of a handle assembly and the medical device assembly during the first stage of deployment.

DETAILED DESCRIPTION OF THE ILLUSTRATED EMBODIMENTS

Figure 1A:
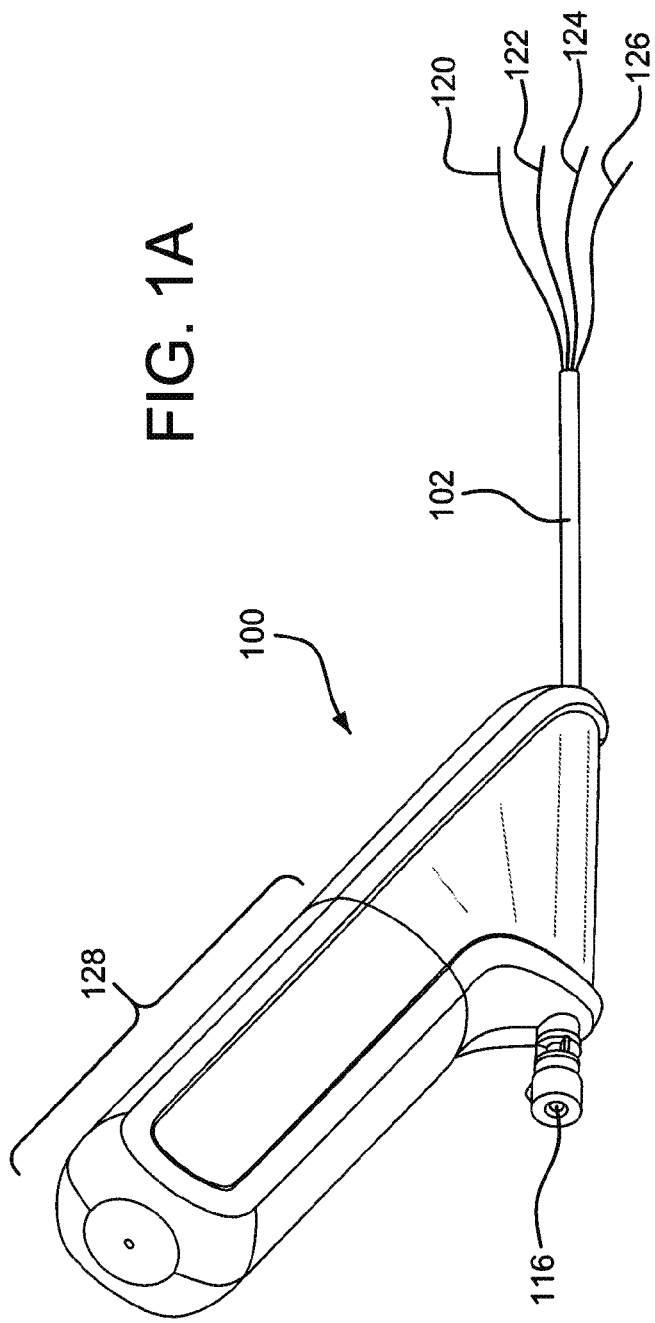
FIGS. 1A and 1B are perspective views of a handle assembly and medical device according to one embodiment of the present invention.

The invention is directed to a handle used to deliver a medical device, wherein the handle aids a practitioner in performing a fixed sequence of activation steps. In its simplest form the handle comprises a first removable member attached to a first distally extending line for communication with a remotely located deployable device; and a second member having an adjustment feature to modulate the deployable device. The second member is at least partially covered by the first removable member and is attached to a second distally extending line for communication with the remotely located deployable device.

Another aspect of the device provides a handle which comprises a first removable member attached to a first distally extending line for communication with a remotely located deployable device; a second removable member having a rotatable portion, the second member at least partially covered by said first removable member and attached to a second distally extending line for communication with the remotely located deployable device; and a third member at least partially covered by said second removable member and attached to a third distally extending line for communication with the remotely located deployable device.

The members may take the form of a removable member and/or movable member. Examples include, but are not limited to, a wire, a covering, a knob, a knob assembly (a knob with additional components within the knob), a pin, cap, lid, sheet cover (e.g. a tape), hook, switch, or other structure for encouraging the order of removal and/or activation of distally extending lines. Said first, second, third or additional members can be a combination of any of the above listed types of members or any other structure. Said members can be attached to distally extending lines. Members can be removed and/or moved by, inter alia, rotation, pulling, pushing, pressing, bending, unsnapping, breaking or any other method of removing and/or moving a member and still be able to activate a distally extending line. In one aspect, said member can cover each other (i.e. nest within other members). In another aspect, said members prevent another member from being removed and/or moved before another member is removed and/or moved. The fixed sequence activation handle may further comprise a port which allows access to at least one of the first, second, third or additional distally extending lines.

In another aspect, the fixed sequence activation handle has at least a first, second and third removable member each attached to a distally extending line in communication with a remotely located deployable device having a first and second portion wherein removal of the first member from the handle results in partial deployment of the first portion of the remotely located deployable device thus allowing access to the second member. The second member can include a rotatable portion wherein rotation of said rotatable portion modulates the first portion of the deployable device and wherein removal of said second member results in complete deployment of the first portion of the device and allows access to the third member. Manipulation of the third member deploys the second portion of the device. In another aspect, the presence of the first member prevents removal and/or moving of the second member. In another aspect, the presence of the second member prevents the removal or moving of the third member. In another aspect, the third member is nested within the second member and the second member is nested within the first member. In another aspect, said removable members can be tethered together for easily accounting for the removed components by the medical/delivery team. In another aspect, a system for placing each removed component in a holder so that the removed member can be readily accounted for is also contemplated.

Also provided is a method of delivering a deployable device comprising the steps of: providing a handle having at least a first, second and third removable member each attached to at least one distally extending line for communication with a remotely located deployable device having a first and second portion; delivering the deployable device to a target location; removing the first member from the handle to partially deploy the first portion of the device and allow access to the second member; rotating a rotatable portion of the second member to modulate the first portion of the deployable device; removing the second member to complete deployment of the first portion of the device and allow access to the third member; and manipulating the third member to deploy the second portion of the device resulting in delivery of the deployed device.

For the illustrative purposes, FIGS. 1 through 7 provide detailed examples of a medical device and delivery sequence. The sequence steps are dictated and fixed by the design of the delivery handle. To add clarity, FIGS. 1 through 7 show the various stages of the handle activation along with a corresponding view of a typical medical device as it is being deployed.

Figure 1B:
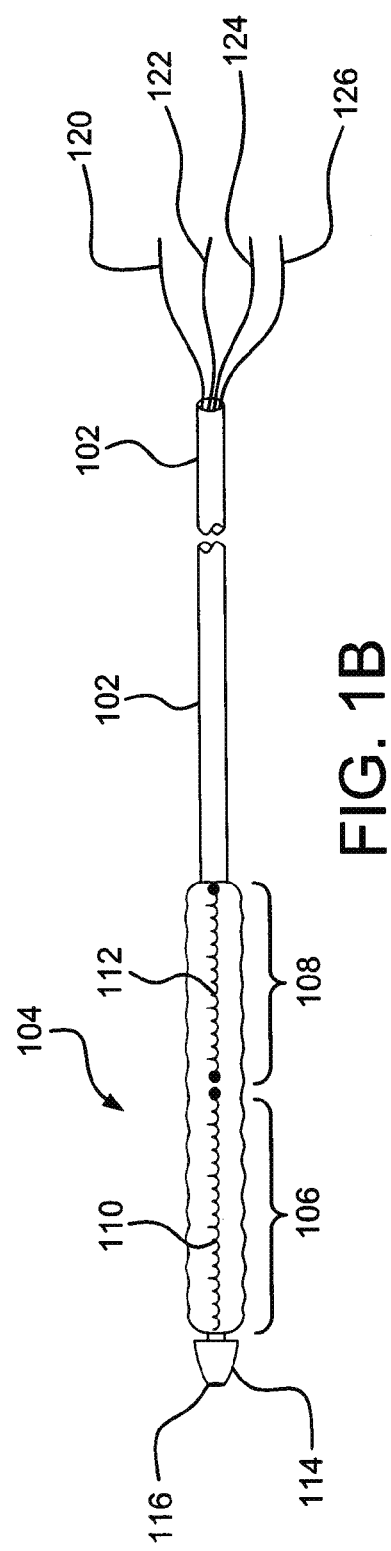

FIGS. 1A and 1B are perspective views of a handle assembly according to one embodiment of the present invention. FIG. 1B is a side view of a medical device to be deployed. Shown (at FIG. 1A) is a handle assembly 100, having a catheter 102. The catheter 102 extends to a medical device assembly 104. A portion of the catheter is shown removed to expose the internal control lines. The medical device shown is a self expanding stent graft that is held in a constrained state by two separate constraining sheaths 106 and 108. Each of the constraining sheaths have a "rip-cord" stitch 110 and 112. Stent grafts and constraining sheaths can be fabricated according to the methods and materials as generally disclosed in, for example, U.S. Pat. No. 6,042,605 issued to Martin, et al., U.S. Pat. No. 6,361,637 issued to Martin, et al. and U.S. Pat. No. 6,520,986 issued to Martin, et al. At the far distal end of the medical device is an olive 114. A guide wire lumen 116 exits the distal end of the olive and extends through the catheter 102 and through the handle 100. A guidewire is typically used during the delivery of the medical device but has been omitted from the Figures for clarity. Contained within the catheter 102, are four individual control lines 120, 122, 124 and 126. These control lines will subsequently be used to affect the deployment of the medical device. Also shown is a first member 128, removably attached to the handle assembly 100.

FIGS. 2A and 2B show perspective views of the handle assembly 100 and the medical device assembly 104 during the first stage of deployment. To affect the first stage of deployment, the first member 128 is rotated according to direction arrow 202 and then pulled along direction arrow 204. Attached to the first member 128 is the first control line 120. When the first member 128 is pulled, the first control line 120 is pulled along direction arrows 206. The first control line 120 "un-stitches" the distal constraining sheath 106 as it is being pulled, allowing the distal portion of the stent graft to self expand in the directions indicated by arrows 208. The first member 128 is pulled until the distal constraining sheath is fully un-stitched. By pulling further on the first member, the first control line 120 is fully removed from the catheter/handle and is discarded. While in the state depicted in FIG. 2, the medical device assembly 104 is still attached to the catheter 102 by the proximal constraining sheath 108. Also while in the state depicted in FIG. 2, the medical device anchors or barbs 210 are in a withdrawn or contracted state.

Figure 3A:
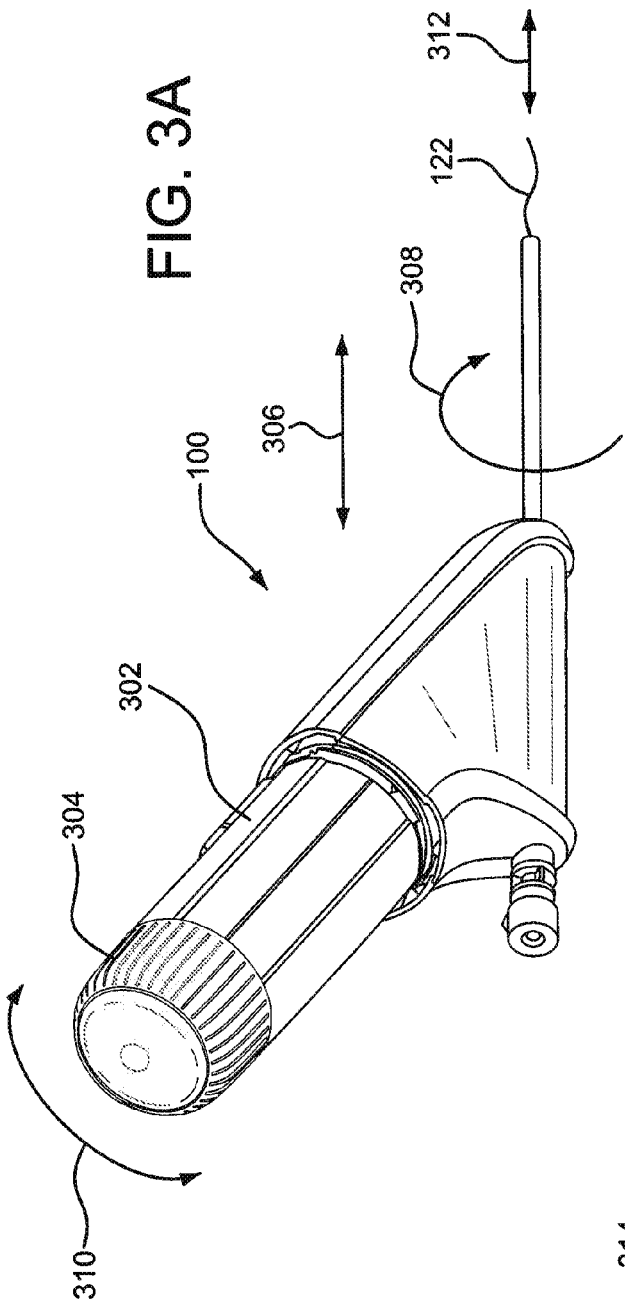
FIGS. 3A and 3B are perspective views of a handle assembly along with a partial side view of the distal portion of the medical device, showing the positional manipulation of the medical device along with the retraction and release of the device anchors.
Figure 3B:
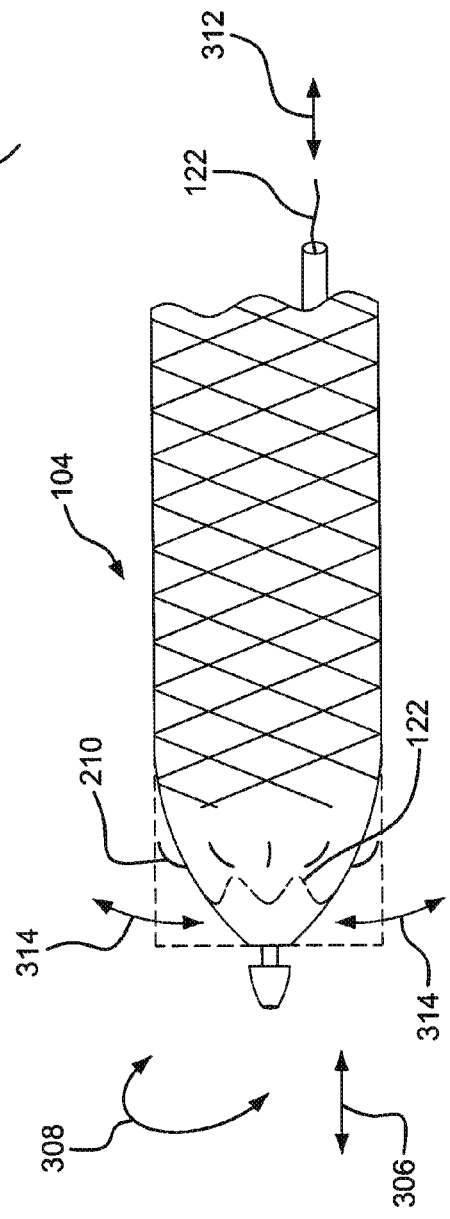

FIG. 3A is a perspective view of the handle assembly 100 along with a partial side view of the distal portion of the medical device 104 (FIG. 3B). When the first member 128 (FIG. 2) was removed a second member 302 was exposed. Fixed to the second member 302 is a rotatable portion 304, in the form of a knob. While in the states shown in FIGS. 2 and 3, the position of the medical device within the vasculature can be precisely adjusted. For example the handle assembly 100 can be translated along direction arrows 306 to move or adjust the medical device in a longitudinal direction 306.

Similarly, the handle can be rotated as indicated by direction arrows 308 to cause a rotation of the medical device. The longitudinal adjustment will allow precise alignment of the medical device to a specific target within the vasculature, for example to a position very close to but not occluding a side branch vessel. The rotational adjustment will also allow precise alignment of a bifurcated or side branched device.

The longitudinal and rotational manipulations of the medical device are possible due to the medical device attachment to the catheter along with the device anchors being in a retracted state. When the medical device is precisely located at the target site, the device anchors can be released and allowed to engage the vascular wall. The release (or retraction) of the anchors is affected by rotating the rotatable portion 304 in the directions indicated by arrow 310. When the rotatable portion 304 is rotated, tension 312 is applied (or removed) to the second control line 122. Control line 122 is routed through the catheter and is then threaded, in a "purse-string" fashion, around the distal anchor portion of the medical device. When tensioned, control line 122 will cause the anchors to retract. When rotatable portion 304 is rotated in an opposite direction, the tension on control line 122 is relaxed, allowing the anchor portion of the device to self expand in the direction indicated by arrows 314, thereby engaging the anchors into the vasculature wall.

Figure 4:
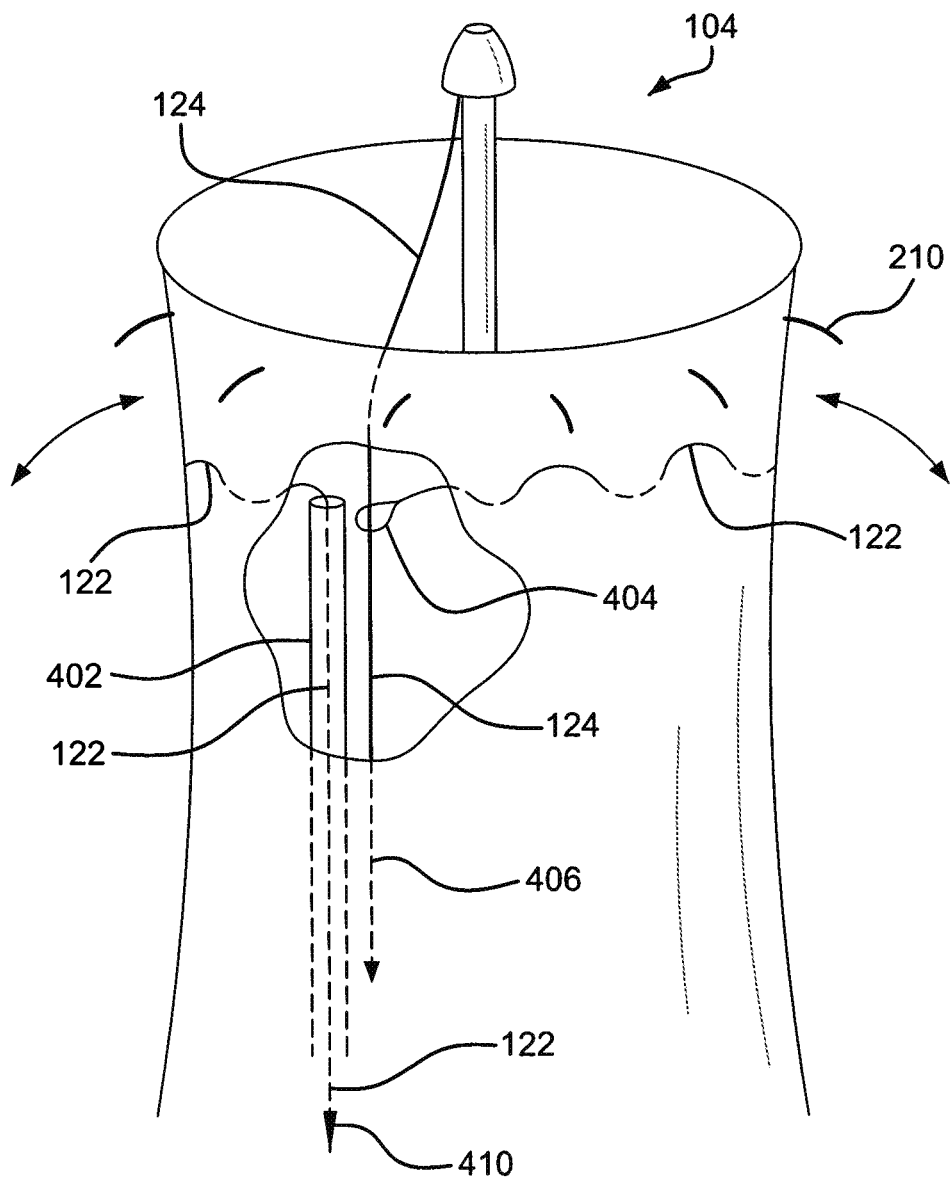
FIG. 4 is a partial perspective view of the distal portion of the self expanding medical device, showing details of the second control line.

After the precise alignment of the medical device and the engagement of the device anchors, the second control line 122 must be removed. Shown in FIG. 4 is a partial perspective view of the distal portion of the self expanding medical device 104, showing details of the second control line 122. The second control line 122 is shown contained within a small tube 402 that is attached to the catheter shaft 102 (not shown). The second control line 122 is shown threaded through the stent graft in a purse-string fashion. The second control line 122 terminates with a loop 404 that is captured by a third control line 124. When the third control line 124 is pulled in the direction indicated by arrow 406, the loop 404 is released, allowing the second control line 122 to be pulled in the direction as indicated by arrow 410. The second control line 122 is then further pulled and remove from the medical device.

Figure 5A:
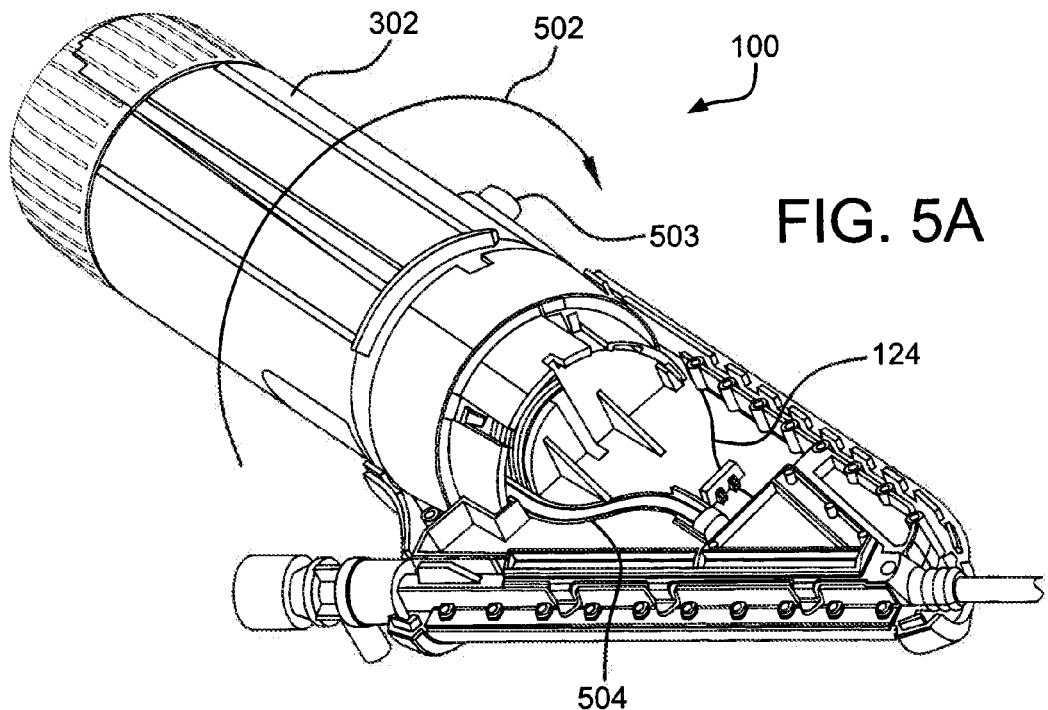
FIGS. 5A and 5B are perspective cut-away views of a handle showing the fixed pulling sequence of the second and third control line.
Figure 5B:
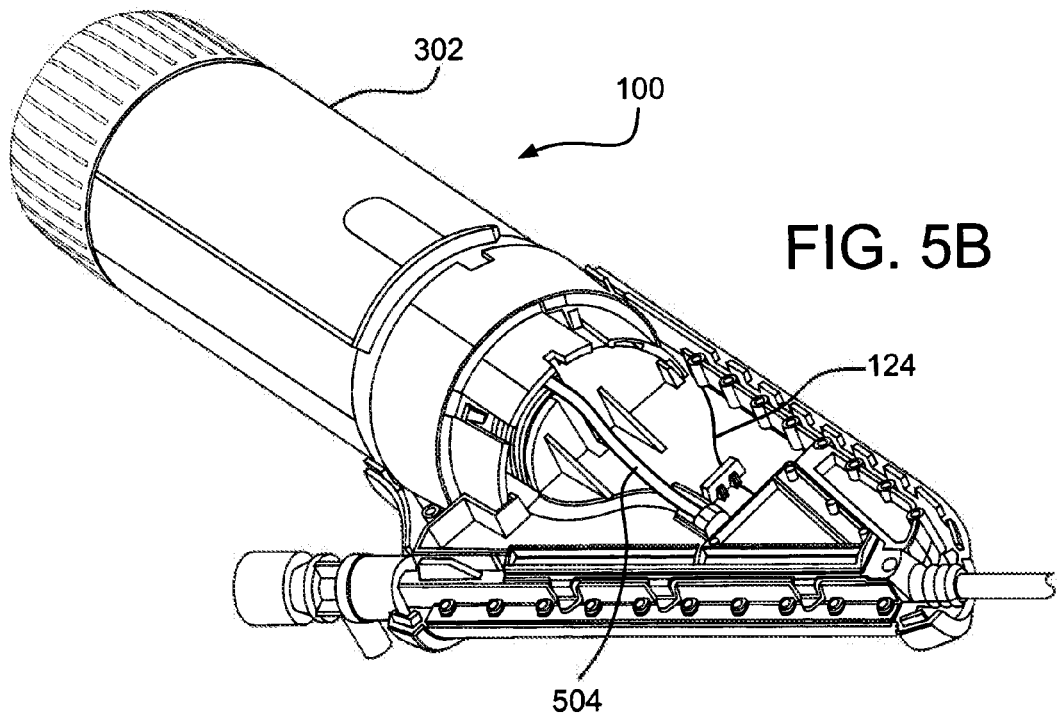

In order to remove the second control line 122 from the medical device, the third control line 124 must be pulled first (to release to second control line loop). This sequence of pulling the two control lines is affected by the handle mechanism depicted in FIGS. 5A and 5B. The third control line 124 is directly attached to the rotatable member 302, so that when member 302 is initially rotated in the direction indicated by arrow 502, the third control line 124 is pulled to release the loop 404 (FIG. 4). In order to rotate member 302 an interlock button 503 must be manually activated. The second control line 122 is contained within a rigid tube 504. Thus when the member 302 is rotated, the rigid tube 504 is rotated as shown in FIG. 5B. The second control line 122 is therefore not further tensioned since the rigid tube maintains a constant length. Therefore the rotation of member 302 will result in a differential motion between the third control line 124 and the second control line 122. After member 302 is fully rotated both control lines 122, 124 can be simultaneously translated. This mechanism can be used to activate more than two control lines.

Figure 6A:
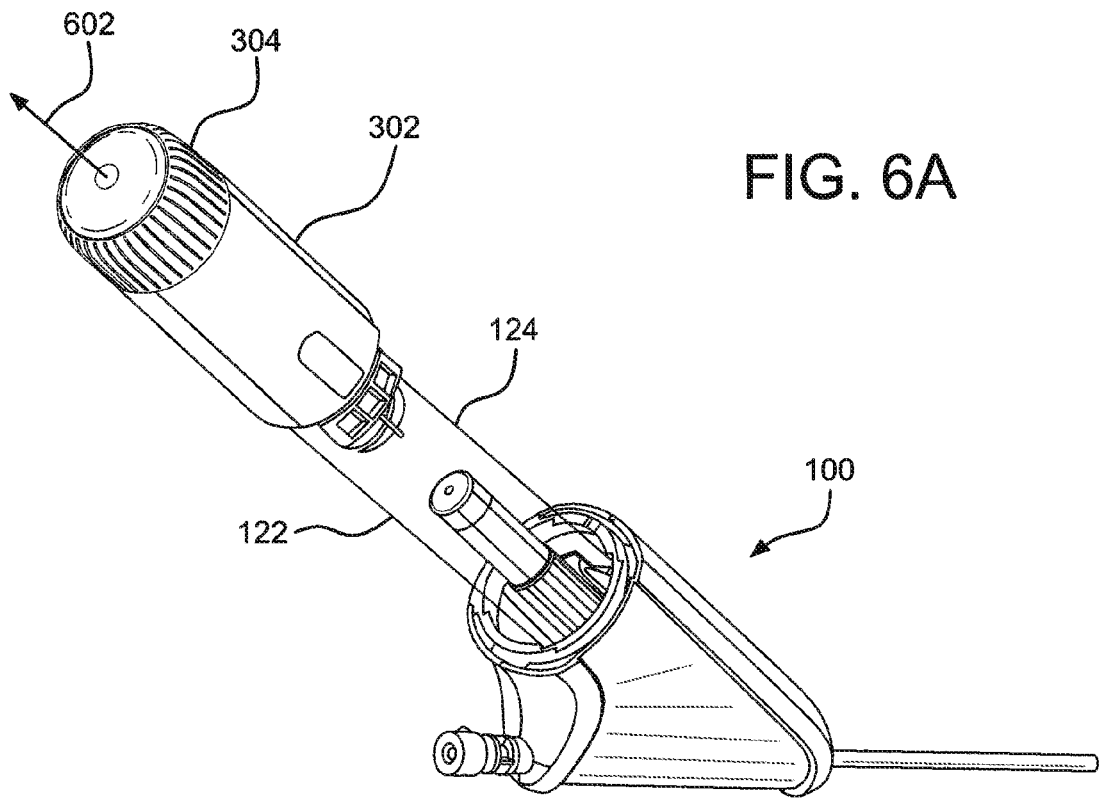
FIGS. 6A and 6B are perspective views of a handle and a side view of the medical device showing the removal of the second and third control lines.
Figure 6B:
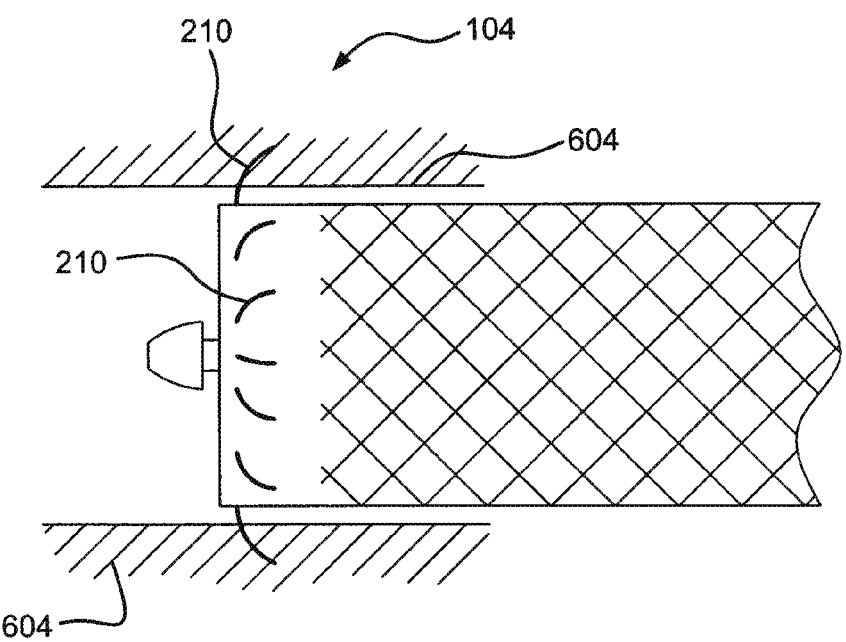

As shown in perspective at FIG. 6A and partial side view at FIG. 6B, the second member 302 with the attached rotatable portion 304 can then be removed by pulling in the direction indicated by arrow 602. As the member 302 and rotatable portion 304 are pulled, the two control lines 122 and 124 are pulled and fully removed from the device, catheter and handle. The member 302 and rotatable portion 304 are interlocked so that they cannot be removed from the handle unless the knob is fully rotated to allow full expansion of the medical device anchors. The knob rotation causes a follower nut to translate to a home position which in turn releases an interlock to allow subsequent removal of the second member 302. Additionally there can be a secondary interlock, such as a button that must be manually activated to allow removal of the second member 302. After complete removal of the second member 302 and any attached control lines the distal portion of the medical device 104, partially shown in FIG. 6, is fully deployed with the anchors 210 fully engaging the vascular wall 604.

Figure 7A:
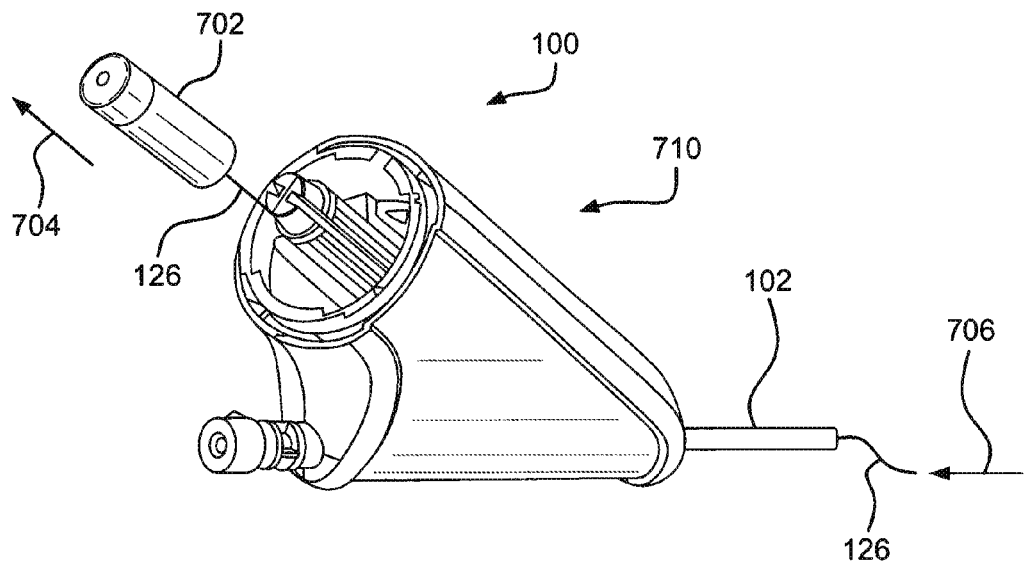
FIGS. 7A and 7B are perspective views of a handle and medical device showing the activation of the fourth control line.
Figure 7B:
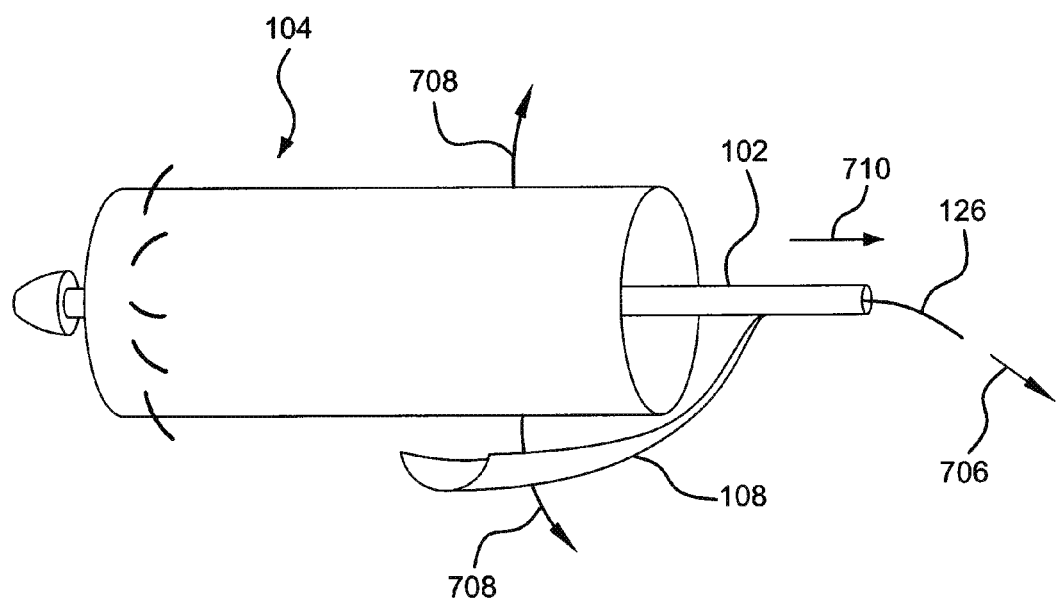

As shown in perspective views of FIGS. 7A and 7B, the second constraining sheath 108 can be released by the removal of a third member 702. The fourth control line 126 is attached to the third member 702, so that when the third member is pulled in the direction indicated by arrow 704, the fourth control line 126 is pulled in the direction indicated by arrow 706. When pulled, the fourth control line 126 "un-stitches" the second constraining sheath 108, allowing the medical device to self expand in the direction as indicated by arrow 708. The third member 702 and attached fourth control line 126 can then be fully removed from the medical device, catheter and handle. The medical device 104 is now fully deployed and is no longer attached to the catheter 102. The handle can therefore be pulled in the direction indicated by arrow 710, removing the catheter from the vasculature and completing the deployment phase of the procedure. The second constraining sheath 108 can be optionally attached to the catheter or be allowed to remain in the vasculature.

Figure 8:
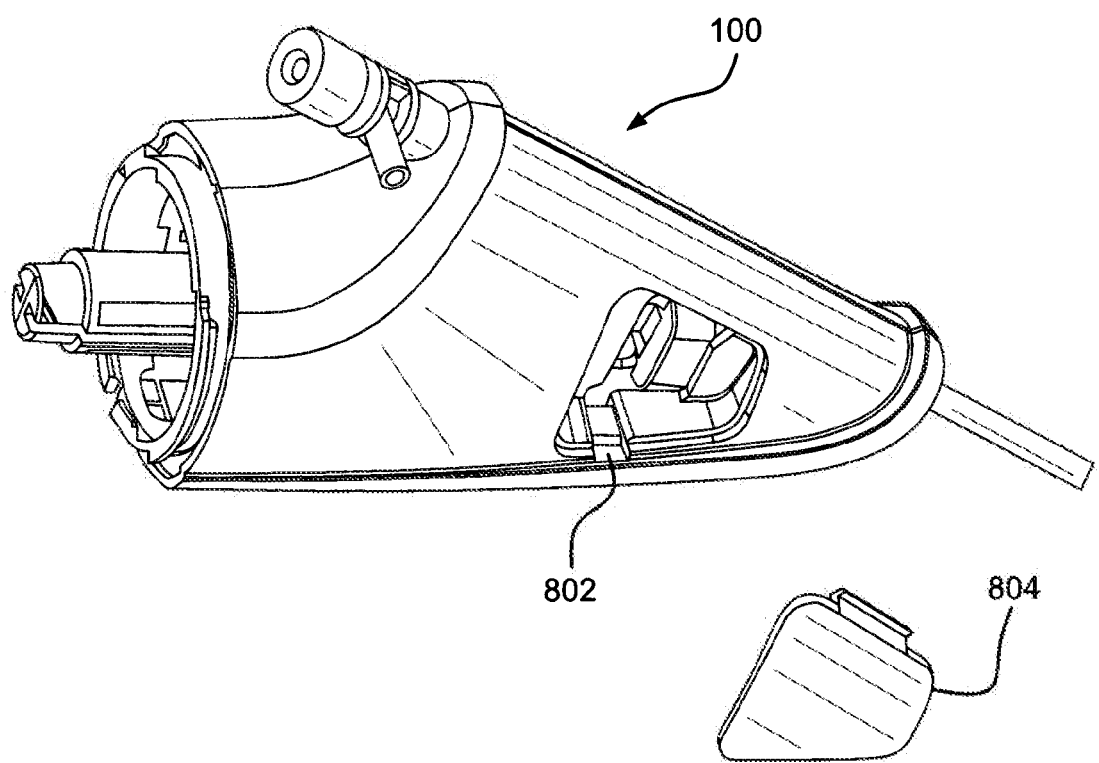
FIG. 8 is a perspective view of a handle showing a safety access portal.

As shown in the perspective view of FIG. 8, the handle assembly 100 can incorporate an access portal 802, allowing manual access to the various control lines if required. The access portal 802 can be exposed if desired by the removal of cover 804. The various control lines can be identified by colors, alpha-numeric markings, ordered locations, different sizes or shapes or any other indentifying means. The control lines can incorporate features to allow grasping and manipulations of the lines by commonly available tools.

The present invention is not limited to the use of members as detailed above. Various other means of providing a forced, interlocked activation sequence are possible. For example the interlocked activation mechanisms can include levers, slide-mechanisms, plugs, sequentially pulled tubes, sequentially released locks. Referring to FIGS. 1 through 7, the present invent broadly provides an interlocked activation system that comprises a first, second and third mechanism each having a pre and post activation state. A first mechanism (first member 128) is in a pre-activation state as shown in FIG. 1 and is in a post-activation state as shown in FIG. 2. A second mechanism (second member 302) is in a pre-activation state as shown in FIG. 3 and is in a post-activation state as shown in FIG. 6. A third mechanism (third member 702) is in a pre-activation state as shown in FIG. 6 and is in a post-activation state as shown in FIG. 7.

The interlocked activation system of the present invention initially allows only the first mechanism to transition from the pre to post activation state; the first mechanism (first member 128) is the only activation mechanism initially exposed and is the only mechanism member capable of being activated.

A transition of the first mechanism from the pre to post activation state allows only the second mechanism to transition from the pre to post activation state; after the first member is removed only the second mechanism (second member 302) is exposed and is member capable of being activated.

A transition of the second mechanism from the pre to post activation state allows only the third mechanism to transition from the pre to post activation state; after the second member is removed, only the third mechanism (third member 702) is exposed and is member capable of being activated.

The present invention is not limited to interlocked sequences that use control lines. For example the concepts of the present invention can include interlocked devices that activate electrical contacts. Such contacts can rely on the conductance of the various handle components so that an electrical contact is opened when a particular handle component is removed. The manipulation of a particular handle component could also activate a simple electrical switch. The manipulation of a particular handle component could also activate proximity sensors, pressure sensors, fluid flow sensors or other type sensors. Combinations of various activators can also be incorporated into the designs of the present invention. For example control lines could be combined with electrical switches. In addition to handles or hand-held pendants, the various concepts of the present invention can also be incorporated into control panel activation devices.

Typical handles, tools or catheters used to deliver medical devices can comprise commonly known materials such as Amorphous Commodity Thermoplastics that include Polymethyl Methacrylate (PMMA or Acrylic), Polystyrene (PS), Acrylonitrile Butadiene Styrene (ABS), Polyvinyl Chloride (PVC), Modified Polyethylene Terephthalate Glycol (PETG), Cellulose Acetate Butyrate (CAB); Semi-Crystalline Commodity Plastics that include Polyethylene (PE), High Density Polyethylene (HDPE), Low Density Polyethylene (LDPE or LLDPE), Polypropylene (PP), Polymethylpentene (PMP); Amorphous Engineering Thermoplastics that include Polycarbonate (PC), Polyphenylene Oxide (PPO), Modified Polyphenylene Oxide (Mod PPO), Polyphenelyne Ether (PPE), Modified Polyphenelyne Ether (Mod PPE),Thermoplastic Polyurethane (TPU); Semi-Crystalline Engineering Thermoplastics that include Polyamide (PA or Nylon), Polyoxymethylene (POM or Acetal), Polyethylene Terephthalate (PET, Thermoplastic Polyester), Polybutylene Terephthalate (PBT, Thermoplastic Polyester), Ultra High Molecular Weight Polyethylene (UHMW-PE); High Performance Thermoplastics that include Polyimide (PI, Imidized Plastic), Polyamide Imide (PAI, Imidized Plastic), Polybenzimidazole (PBI, Imidized Plastic); Amorphous High Performance Thermoplastics that include Polysulfone (PSU), Polyetherimide (PEI), Polyether Sulfone (PES), Polyaryl Sulfone (PAS); Semi-Crystalline High Performance Thermoplastics that include Polyphenylene Sulfide (PPS), Polyetheretherketone (PEEK); and Semi-Crystalline High Performance Thermoplastics, Fluoropolymers that include Fluorinated Ethylene Propylene (FEP), Ethylene Chlorotrifluroethylene (ECTFE), Ethylene, Ethylene Tetrafluoroethylene (ETFE), Polychlortrifluoroethylene (PCTFE), Polytetrafluoroethylene (PTFE), Polyvinylidene Fluoride (PVDF), Perfluoroalkoxy (PFA). Other commonly known medical grade materials include elastomeric organosilicon polymers, polyether block amide or thermoplastic copolyether (PEBAX) and metals such as stainless steel and nickel/titanium alloys.

Typical methods used in the assembly of handles include commonly known techniques used to attach two or more components. Examples of permanent attachments include the use of glues, adhesives, welds, insert molding, heavy press-fits, one-way snap or lock features, pressed pins, heat staking and rivets. Examples of semi-permanent attachments or those that require a tool to separate the components include screws, threaded fasteners, snap-rings and snap-fits. Examples of releasable attachments or those that can be separated by hand without the use of an additional tool include snap-fits, twist lock features, push to release features, squeeze to release features, slide levers, latches and light press-fits.

Control lines can comprise commonly known high tensile strength materials such as carbon fibers, liquid crystal polymers and metal wires. Control lines can have various cross-sectional profiles such as circular, oval, rectangular or other polygon shapes. Control lines can also incorporate external lubricious layers, lubricious coatings or lubricious wrappings to minimize friction.

Control lines can be attached to handle or activation mechanisms by a variety of commonly know methods such as wrapping a control line around a pin or by securing a line by screws. Other methods include threading a line through a small hole and then tying knots or securing a protuberance to the end of the control line so that the knot/protuberance cannot be pulled through the small hole. Adhesives, clamps, crimps, pinch mechanisms, heat staking, insert molding and other common attachment methods could also be used for control line attachments. Alternatively, a control line or cable retention system may be used to secure the wires inside the handle. The system comprises at least one retaining element; a substrate having a cavity dimensioned to allow an insertion of the at least one retaining element; a first slot extending from a first edge of the substrate to said cavity; and a second slot extending from a second edge of the substrate to said cavity wherein the first and second slots are dimensioned to allow a placement of an elongate member, such as a wire, within the slots so that the retaining element retains the elongate member in the cavity. The retaining element may be a ball bearing, a spherical element, a cylindrical post, or other such means used to deform the elongate member. The cavity extends to a depth below that of the depth of the first and second slot to create a space in which to deflect or deform the wire into using the retaining element. The cavity may be of any suitable dimension of shape or size so that a retaining element may secure the wire into the substrate cavity. It is desired to provide a cavity diameter that is smaller than that of the retaining element to allow a force fit. If desired an adhesive may be placed in the cavity prior to and/or after deforming the wire into the cavity so that an added securement means is provided. In order to retain an elongate member such as a wire in a device the following steps may be utilized. A device handle having a substrate with a cavity, a first slot and a second slot is obtained such as shown in FIG. 9A-9F. At least one elongate member is positioned within the first and second slot to cross the cavity. At least one retaining element is positioned within the cavity so that the at least one elongate member is secured between the retaining element and the substrate. The elongate member is deformed by the retaining element such that it is secured in position between the retaining element and the substrate.

Figure 9A:
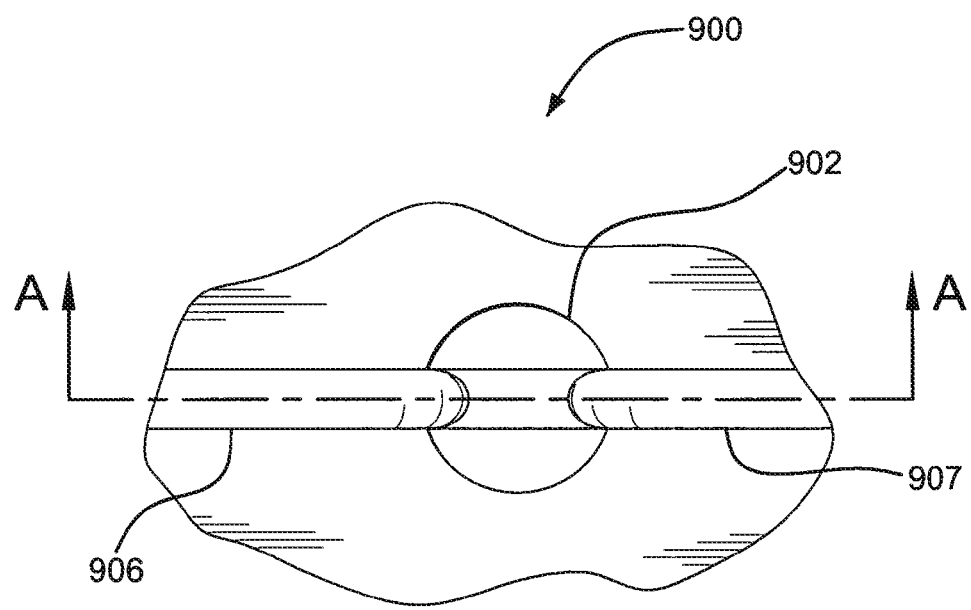
FIGS. 9A through 9F show partial top and partial side cross-sectional view of a device and method used to secure a control line to an attachment feature or substrate.
Figure 9B:
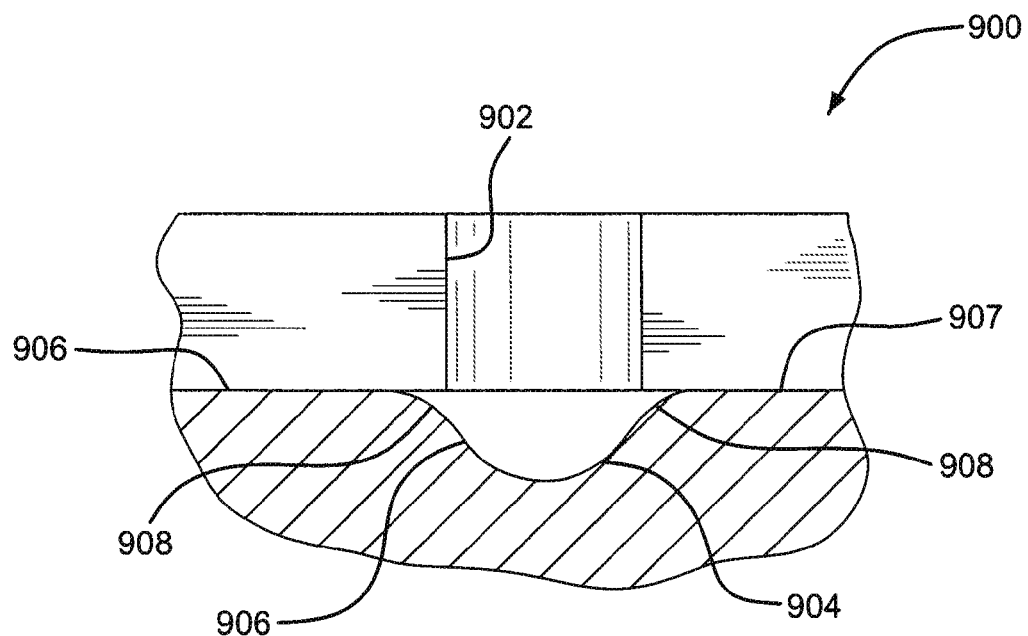

This simple, easy to assemble, easily automatable, visually verifiable and high strength joining concept is disclosed in FIGS. 9A through 9F. Shown in FIG. 9A is a partial top view of a control line attachment feature 900 while FIG. 9B displays a partial cross-sectional side view taken along plane A-A. Shown is a circular cavity 902 terminating in a spherical shape 904. A first slot 906 and a second slot 907 have been formed through the attachment feature and penetrate the circular hole. The slots 906 and 907 are shown as centered on the cavity 902 centerline. The slots may optionally be located at non-centered positions on the cavity. As shown in FIG. 9B, optionally, the slot 906 "dives into" the edges 908 of the circular bottom of the cavity 902, forming a curved channel when viewed along cross-sectional plane A-A.

Figure 9C:
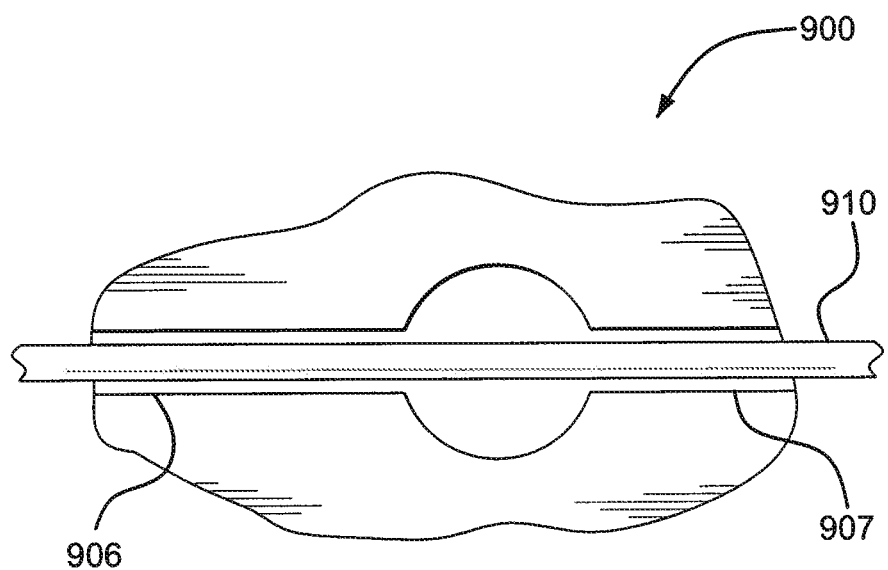
Figure 9D:
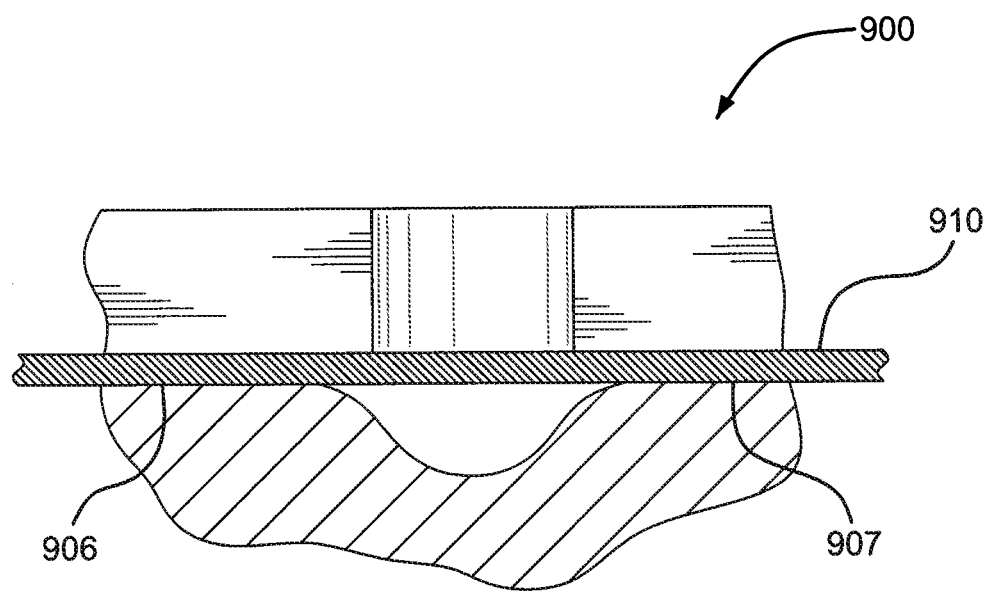
Figure 9E:
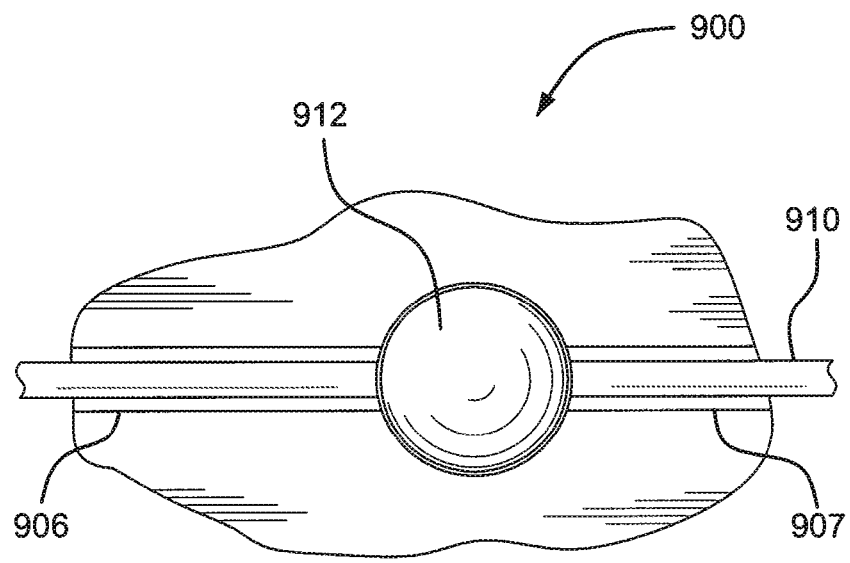
Figure 9F:
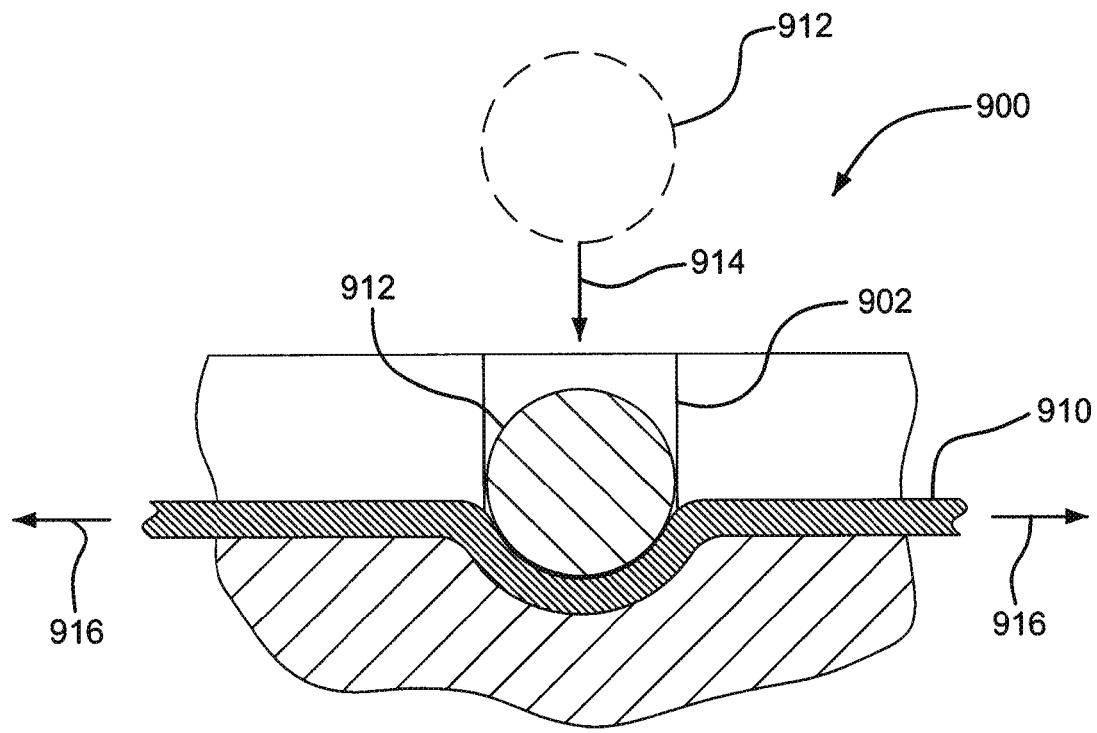

As shown in FIGS. 9C and 9D, a control line 910 is placed into the first slot 906. Referring to FIGS. 9E and 9F, to secure and fix the control line to the attachment feature, a retaining element 912 is pressed into the cavity 902 along the direction indicated by arrow 914. When fully seated the rigid sphere deforms the control line into the shape of the curved channel. The interference, press fit between the cavity 902, and the retaining element 912 effectively secures the control line onto the attachment feature. The control line can then be bi-directionally tensioned 916 without slipping or dislodging from the attachment feature. If desired, an adhesive can be applied to the exposed portion of the rigid sphere to further enhance the retention of the control line. Optionally, the exposed portion of the cavity can also be "heat-staked" or deformed to further constrain the rigid sphere and control line. Optionally, the cavity 902 can incorporate retaining element alignment guides such as raised vertical shoulders, chamfers, funnels or other means to align the retaining element to the hole.

The attachment feature 900 can be fabricated from commonly known plastics or metals as listed above. The retaining element 912 can be a metallic ball bearing, a plastic sphere or a ceramic/glass sphere. A rigid roller or cylinder shaped element can be used in place of the rigid sphere to secure ribbon shaped control lines. Other rigid element shapes and matching holes can be used to attach various elements together as desired. A rigid element can also be transparent to allow visual inspections.

Attachment features of the present invention can also be used to secure electrically conductive materials such as wires or cables. Attachment features of the present invention can also be used to secure non-electrically conductive materials such as fiber optics, silks, polymers or natural bio-materials such as blood vessels or nerves.

The attachment feature can also be used to release a cord or cable at a predetermined load. For example the attachment feature substrate, cable, and retaining element can have various tolerances, a specific hardness or specific surface features that, in combination, result in a pre-determined retention load.

EXAMPLES

Example 1

Figure 10A:
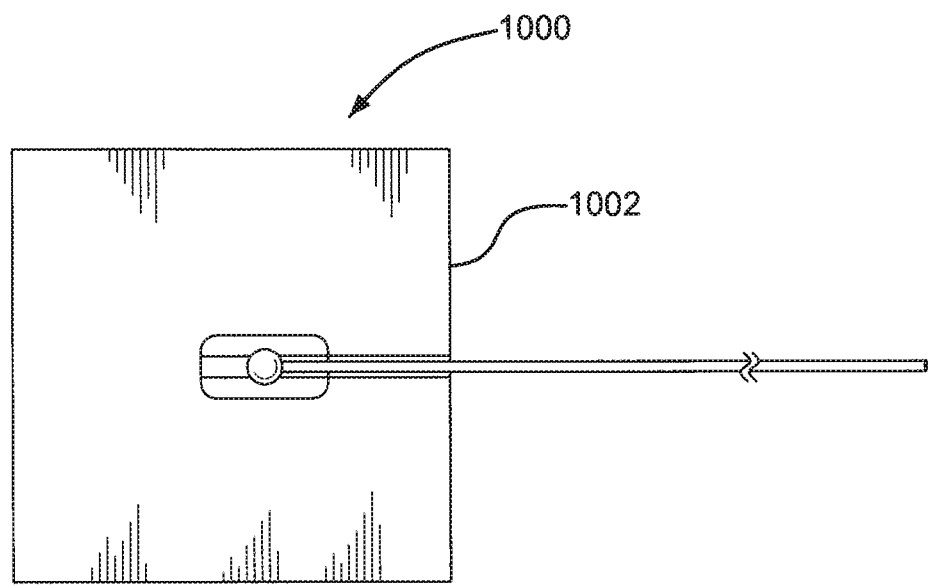
FIGS. 10A through 10D show top, perspective and cross-sectional views of a test fixture used to evaluate a retention feature of the present invention.
Figure 10B:
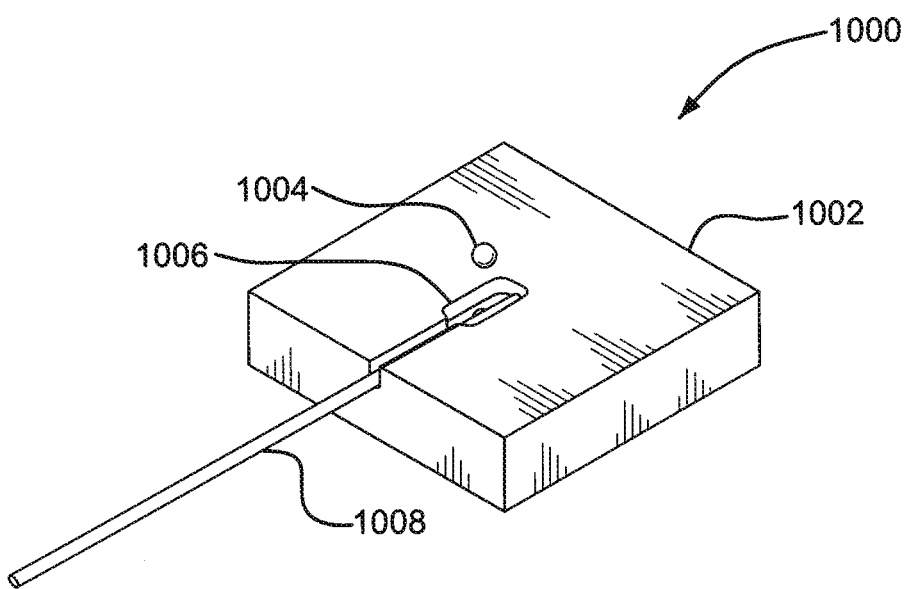
Figure 10C:
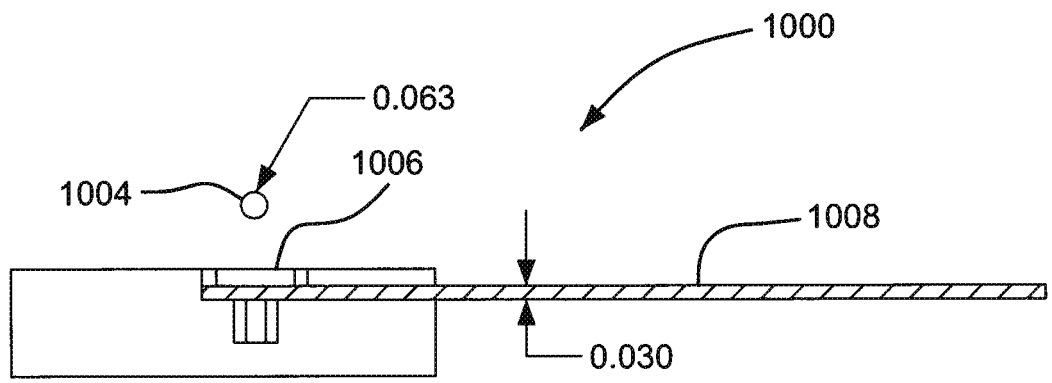
Figure 10D:
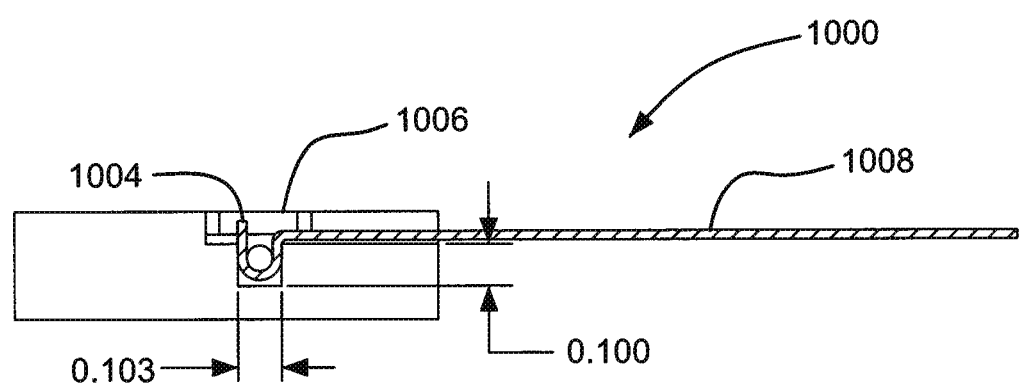

A fixture, according to one embodiment of the present invention, was fabricated to test cable retention forces. As shown in top view FIG. 10A and perspective view 10B, an attachment feature 1000 was assembled having a substrate 1002. The substrate 1002 had a cavity 1006, sized to accept a cable 1008 and a retention sphere 1004. FIGS. 10C and 10D are sectional views taken along the centerline of cavity 1006. As shown, a cable 1008 was placed into the cavity 1006. A ball bearing 1004 was then pressed into the cavity 1006, deforming the cable as shown in FIG. 10D. A medical grade UV curable adhesive was then dispensed into the cavity, partially enmembersulating the cavity, ball bearing and the deformed cable.

Example 2

The fixture from Example 1 was fitted with cable sections, ball bearings were pressed into the cavities and an adhesive was applied as an overcoat. The compressive loads required to press and seat the ball bearings were recorded using an Ametek® (Paoli, Pa.) Chatillion® DFX-050 compression gage. After curing the adhesive, the cables were tensioned to determine the retention load. The cables were tensioned using an Instron® (Norwood, Mass.) tensile tester and load cell. Twenty assemblies were evaluated.

While particular embodiments of the present invention have been illustrated and described herein, the present invention should not be limited to such illustrations and descriptions. It should be apparent that changes and modifications may be incorporated and embodied as part of the present invention within the scope of the following claims.

What is claimed is:

1. A fixed sequence activation handle comprising:
   a first removable member attached to a first distally extending line for communication with a remotely located deployable device;
   a second removable member having a rotatable portion, the second member at least partially covered by said first removable member and attached to a second distally extending line for communication with the remotely located deployable device; and
   a third member at least partially covered by said second removable member and attached to a third distally extending line for communication with the remotely located deployable device,
   wherein the third distally extending line maintains communication between the second distally extending line and the deployable device,
   wherein rotation of said rotatable portion modulates a first portion of the deployable device without causing axial displacement of the rotatable portion relative to the second member.

2. The fixed sequence activation handle of claim 1, wherein the presence of the first member prevents the removal of the second member.

3. The fixed sequence activation handle of claim 1, wherein the presence of the second member prevents the removal of the third member.

4. The fixed sequence activation handle of claim 1, wherein the third member is nested within the second member; and the second member is nested within the first member.

5. The fixed sequence activation handle of claim 1, wherein the third member is removable.

6. The fixed sequence activation handle of claim 1, further comprising an access port to at least one of said first, second or third distally extending lines.

7. The fixed sequence activation handle of claim 1, wherein the second member comprises an adjustment feature.

8. A fixed sequence activation handle comprising:
   at least a first, second and third removable member each attached to a distally extending line in communication with a remotely located deployable device having a first and second portion,
   wherein removal of the first member from the handle results in partial deployment of the first portion of the device and allows access to the second member,
   wherein the second member includes a rotatable portion wherein rotation of said rotatable portion modulates the first portion of the deployable device without causing axial displacement of the second removable member,
   wherein removal of said second member results in complete deployment of the first portion of the device and allows access to the third member, and
   wherein manipulation of the third member deploys the second portion of the device.

9. A method of delivering a deployable device comprising the steps of:
   providing a handle having at least a first, second and third removable member each attached to at least one distally extending line for communication with a remotely located deployable device having a first and second portion;

delivering the deployable device to a target location;

removing the first member from the handle to partially deploy the first portion of the device and allow access to the second member;

rotating a rotatable portion of the second member to modulate the first portion of the deployable device without causing axial displacement of the second removable member;

removing the second member to complete deployment of the first portion of the device and allow access to the third member; and manipulating the third member to deploy the second portion of the device resulting in delivery of the deployed device.

10. A fixed sequence activation handle comprising:

a first removable member attached to a first distally extending line for communication with a remotely located deployable device; and a second removable member having a rotatable portion, the second member at least partially covered by said first removable member and attached to a second distally extending line and a third distally extending line each for communicating with the remotely located deployable device, the third distally extending line maintaining communication between the second distally extending line and the deployable device, wherein rotation of said rotatable portion modulates a first portion of the deployable device via axial displacement of the second distally extending line without causing axial displacement of the third distally extending line.

11. The fixed sequence activation handle of claim 10, wherein the second and third distally extending lines are operatively coupled so as to be removable concurrently with the removal of the second removable member from the fixed sequence activation handle.

* * * * *